United States Patent
Say

(10) Patent No.: US 9,097,652 B2
(45) Date of Patent: Aug. 4, 2015

(54) SENSOR ARRAY MOUNTED ON FLEXIBLE CARRIER

(75) Inventor: James L. Say, Breckenridge, CO (US)

(73) Assignee: Pepex Biomedical, Inc., St. Louis, MO (US)

( * ) Notice: Subject to any disclaimer, the term of this patent is extended or adjusted under 35 U.S.C. 154(b) by 0 days.

(21) Appl. No.: 13/978,307

(22) PCT Filed: Jan. 5, 2012

(86) PCT No.: PCT/US2012/020342
§ 371 (c)(1),
(2), (4) Date: Oct. 17, 2013

(87) PCT Pub. No.: WO2012/094502
PCT Pub. Date: Jul. 12, 2012

(65) Prior Publication Data
US 2014/0027311 A1     Jan. 30, 2014

Related U.S. Application Data

(60) Provisional application No. 61/430,393, filed on Jan. 6, 2011.

(51) Int. Cl.
*G01N 27/327* (2006.01)
*G01N 27/30* (2006.01)

(52) U.S. Cl.
CPC ............ *G01N 27/30* (2013.01); *G01N 27/3272* (2013.01)

(58) Field of Classification Search
CPC .................................................. G01N 27/3272
USPC ............. 204/403.01–403.15; 205/777.5, 778, 205/792
See application file for complete search history.

(56) References Cited

U.S. PATENT DOCUMENTS

| | | |
|---|---|---|
| 3,823,035 A | 7/1974 | Sanders |
| 4,255,487 A | 3/1981 | Sanders |
| 4,545,835 A | 10/1985 | Gusack et al. |
| 4,704,311 A | 11/1987 | Pickering et al. |
| 5,262,035 A | 11/1993 | Gregg et al. |
| 5,264,105 A | 11/1993 | Gregg et al. |
| 5,320,725 A | 6/1994 | Gregg et al. |

(Continued)

FOREIGN PATENT DOCUMENTS

| | | |
|---|---|---|
| WO | WO 2010/056869 | 5/2010 |
| WO | WO 2010/056876 | 5/2010 |
| WO | WO 2010/056878 | 5/2010 |

OTHER PUBLICATIONS

International Search Report and Written Opinion from International Application No. PCT/US2012/020342 mailed Aug. 24, 2012.

*Primary Examiner* — Alexander Noguerola
(74) *Attorney, Agent, or Firm* — Merchant & Gould P.C.

(57) ABSTRACT

A sensor apparatus is disclosed herein. The sensor apparatus includes a flexible carrier that is elongated along a length of the carrier. The sensor apparatus also includes a plurality of analysis zones carried by the carrier. The analysis zones are spaced-apart from one another along the length of the carrier. The sensor apparatus further includes first and second spaced-apart electrodes carried by the flexible carrier. The first and second electrodes have lengths that extend along the length of the carrier. At least one of the first and second electrodes includes analyte sensing chemistry. The first and second electrodes extending across and contact the plurality of analysis zones.

9 Claims, 8 Drawing Sheets

(56) References Cited

U.S. PATENT DOCUMENTS

| | | |
|---|---|---|
| 5,356,786 A | 10/1994 | Heller et al. |
| 5,395,504 A * | 3/1995 | Saurer et al. ............ 204/403.03 |
| 5,575,403 A | 11/1996 | Charlton et al. |
| 6,379,317 B1 | 4/2002 | Kintzig et al. |
| 6,464,849 B1 | 10/2002 | Say et al. |
| 6,560,471 B1 | 5/2003 | Heller et al. |
| 6,893,545 B2 | 5/2005 | Gotoh et al. |
| 7,299,081 B2 | 11/2007 | Mace et al. |
| 2003/0146110 A1 | 8/2003 | Karinka et al. |
| 2009/0078586 A1 | 3/2009 | Heller et al. |
| 2010/0204554 A1 | 8/2010 | Say et al. |

\* cited by examiner

SENSOR ARRAY MOUNTED ON FLEXIBLE CARRIER

This application is a National Stage Application of PCT/US2012/020342, filed 5 Jan. 2012, which claims benefit of Ser. No. 61/430,393, filed 6 Jan. 2011 in the USA and which applications are incorporated herein by reference. To the extent appropriate, a claim of priority is made to each of the above disclosed applications.

TECHNICAL FIELD

The present disclosure relates generally to sensors. More particularly, the present disclosure relates to sensors for measuring bio-analyte concentrations in blood samples.

BACKGROUND

Electrochemical bio-sensors have been developed for sensing (e.g., detecting or measuring) bio-analyte concentrations in fluid samples. For example, U.S. Pat. Nos. 5,264,105; 5,356,786; 5,262,035; 5,320,725; and 6,464,849, which are hereby incorporated by reference in their entireties, disclose wired enzyme sensors for sensing analytes, such as lactate or glucose. Wired enzyme sensors have been widely used in blood glucose monitoring systems adapted for home use by diabetics to allow blood glucose levels to be closely monitored. Other example types of blood glucose monitoring systems are disclosed by U.S. Pat. Nos. 5,575,403; 6,379,317; and 6,893,545.

SUMMARY

One aspect of the present disclosure relates to a wired enzyme sensor system that allows for low cost manufacturing and facilitates miniaturization.

Another aspect of the present disclosure relates to a wired enzyme sensor system conducive for continuous automated manufacturing using fiber sensor technology.

A further aspect of the present disclosure relates to a sensor system that allows for enhanced manufacturing control to provide better accuracy and repeatability.

Still another aspect of the present disclosure relates to a sensor system including a plurality of sample fluid analysis zones carried on an elongated, flexible dielectric carrier (e.g., a tape, sheet, film, web, layer, substrate, media etc.). The analysis zones are spaced-apart from one another along a length of the carrier and are separated from each other by gaps. Capillary flow promoting structures can be provided at each of the analysis zones for encouraging a sample fluid (e.g., blood) to flow into the analysis zone by capillary action. Two elongated electrodes extend along the length of the carrier. The electrodes each traverse the gaps between the analysis zones and contact each of the analysis zones. One of the electrodes can include a working electrode and the other of the electrodes can include a reference electrode or a counter/reference electrode. To test a fluid sample for an analyte concentration, one of the analysis zones is wetted with the fluid sample and the electrodes contacting the analysis zone are used to generate a reading indicative of the analyte concentration. After the analyte concentration has been determined and another sample is desired to be analyzed, the electrodes are severed at a location between the used analysis zone and the unused analysis zone(s) to electrically isolate the used analysis zone from the portions of the electrodes contacting the unused analysis zone(s). Thereafter, a reading can be taken at the next unused analysis zone. This process can be repeated until all of the analysis zones carried by the carrier have been used to test fluid samples.

A variety of additional aspects will be set forth within the description that follows. The aspects can relate to individual features and to combinations of features. It is to be understood that both the foregoing general description and the following detailed description are exemplary and explanatory only and are not restrictive of the broad concepts upon which the embodiments disclosed herein are based.

DETAILED DESCRIPTION

Figure 1:
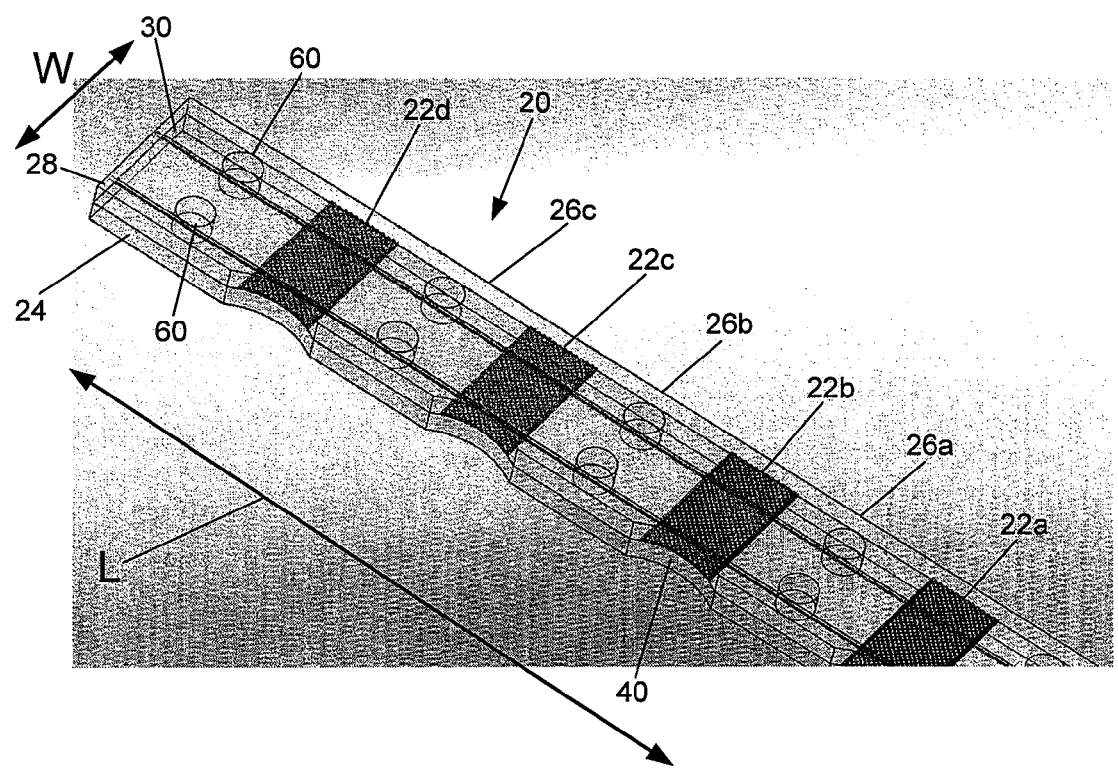
FIG. 1 is a perspective view of a sensor array and flexible carrier in accordance with the principles of the present disclosure.

Reference will now be made in detail to exemplary aspects of the present disclosure which are illustrated in the accompanying drawings. Wherever possible, the same reference numbers will be used throughout the drawings to refer to the same or like parts.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are converted (e.g., transduced) to an electrical signal that can be correlated to an amount, concentration, or level of an analyte in the sample. Further details about electrochemical sensing systems, working electrodes, counter electrodes and reference electrodes can be found at U.S. Pat. No. 6,560,471, the disclosure of which is hereby incorporated herein by reference in its entirety.

"Electrolysis" is the electrooxidation or electroreduction of a compound either directly at an electrode or via one or more electron transfer agents.

An "electron transfer agent" is a compound that carries electrons between the analyte and the working electrode either directly or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both.

FIGS. 1-4 illustrate a sensor array 20 in accordance with the principles of the present disclosure. The sensor array 20 includes a plurality of sample fluid analysis zones 22a-22d carried on an elongated, flexible dielectric carrier 24 (e.g., a tape, sheet, film, web, layer, substrate, media etc.). The analysis zones are spaced-apart from one another along a length L of the carrier 24 and are separated from each other by gaps 26a-26c. Two elongated electrodes 28, 30 extend along the length L of the carrier 24. The electrodes 28, 30 each traverse the gaps between the analysis zones and contact each of the analysis zones. One of the electrodes 28, 30 can include a working electrode and the other of the electrodes 28, 30 can include a reference electrode or a counter/reference electrode.

While, for illustration purposes, only four fluid analysis zones are shown at FIG. 1, it will be appreciated that in preferred embodiments many more than four analysis zones will be provided on each carrier. For example, in certain embodiments, at least 25, or at least 50, or at least 75, or at least 100 analysis zones can be provided on each carrier.

Figure 2:
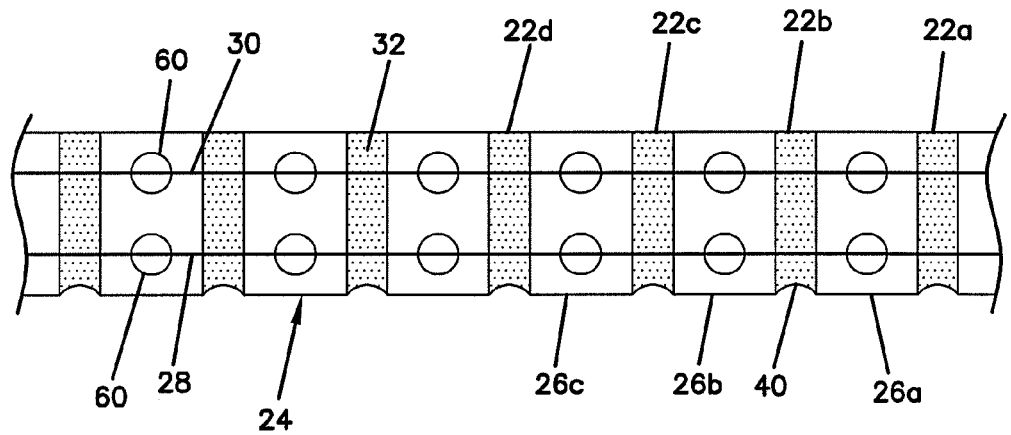
FIG. 2 is a plan view of the sensor array and flexible carrier of FIG. 1.
Figure 3:
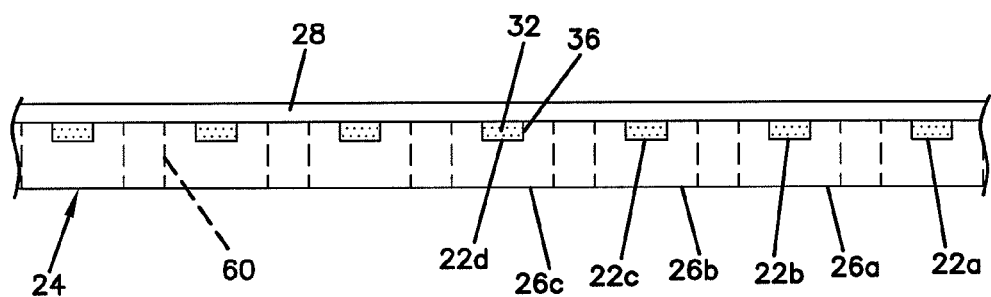
FIG. 3 is a side view of the sensor array and flexible carrier of FIG. 1.

Capillary flow promoting structures can be provided at each of the analysis zones for encouraging a sample fluid (blood) to flow into/across the analysis zone by capillary action. Capillary flow can be in a direction that extends across a width W of the carrier 24. As shown at FIGS. 1-3, capillary flow promoting structures 32 can be provided within wells 36 defined by the carrier 24 at each analysis zone. The capillary flow promoting structures 32 can include cast-in-place foam (e.g., open cell foam), ribbon filter media, capillary yearn or other capillary flow inducing material. The capillary flow promoting structures 32 can also include surface texturing provided on the carrier 24. The capillary flow promoting structures 32 can also include hematocrit filters. Indentations 40 can be provided in the side of the carrier 24 at each of the analysis zones to provide a capillary flow director profile. Prior to use, the analysis zones are preferably dry and not electrically conductive.

Figure 4:
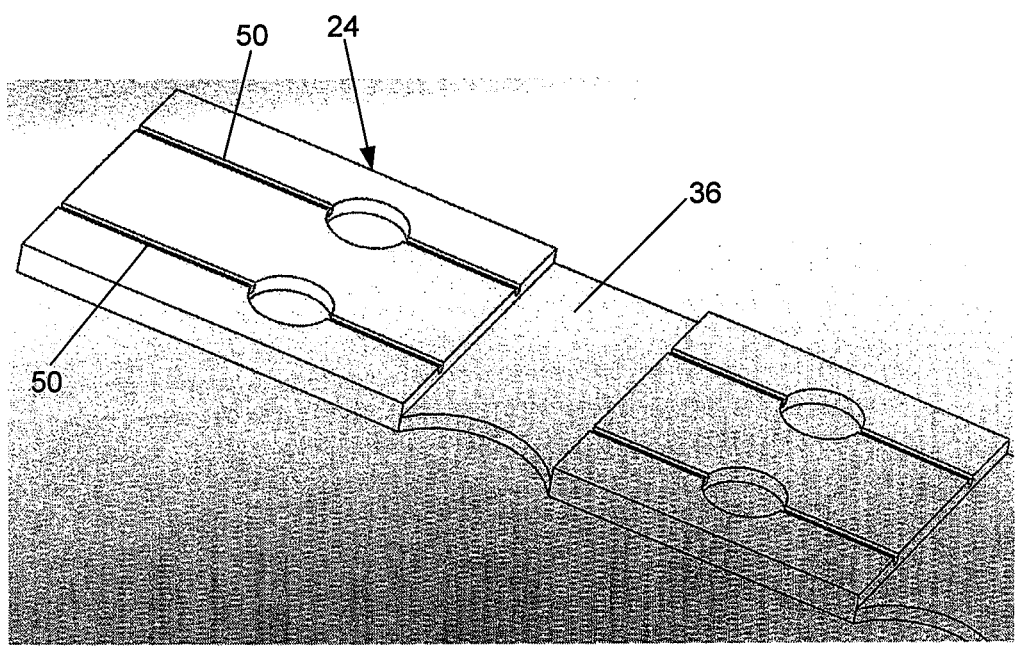
FIG. 4 shows a portion of a flexible carrier of FIG. 1 with other components removed.

The carrier 24 includes structures for mounting the electrodes 28, 30 to the top side of the carrier 24. As shown at FIG. 4, such structures can include grooves 50 in which the electrodes 28, 30 are affixed (e.g., adhesively affixed).

As described later in the description, during use of the sensor array 20 it is desirable to sever (i.e., break, disrupt, interrupt, cut) the electrodes 28, 30 at the gaps. The electrodes can be mechanically severed or severed using other means such as a laser. A preferred method for severing the electrodes at the gaps is to use a punching process. To accommodate a punching process, punch holes 60 are provided at each of the gaps. The electrodes 28, 30 traverse the punch holes 60.

The carrier 24 is preferably made of a dielectric material and is preferably relatively flexible. In one embodiment, the carrier 24 can be wrapped in a cylinder having a diameter less than or equal to 3 inches without breaking. In another embodiment, the carrier 24 can be wrapped in a cylinder having a diameter less than or equal to 2 inches without breaking.

In one embodiment, the electrode 28 is in contact with a sensing layer and functions as a working electrode and the electrode 30 can function as a reference/counter electrode. In other embodiments, separate working, reference and counter electrodes can be provided in fluid communication with the analysis zones. The electrodes 28, 30 are preferably threads, fibers, wires, or other elongated members.

In one embodiment, the working electrode can include an elongated member that is coated or otherwise covered with a sensing layer and the reference/counter electrode can include any elongated member, such as a wire or fiber that is coated or otherwise covered with a layer, such as silver chloride. Preferably, at least a portion of each elongated member is electrically conductive. In certain embodiments, each elongated member can include a metal wire or a glassy carbon fiber. In still other embodiments, each elongated member can each have a composite structure and can include a fiber having a dielectric core surrounded by a conductive layer suitable for forming an electrode.

A preferred composite fiber is sold under the name Resistat® by Shakespeare Conductive Fibers LLC. This composite fiber includes a composite nylon, monofilament, conductive thread material made conductive by the suffusion of about a 1 micron layer of carbonized nylon isomer onto a dielectric nylon core material. The Resistat® material is comprised of isomers of nylon to create the basic two layer composite thread. However, many other polymers are available for the construction, such as: polyethylene terephthalate, nylon 6, nylon 6,6, cellulose, polypropylene cellulose acetate, polyacrylonitrile and copolymers of polyacrylonitrile for a first component and polymers such as of polyethylene terephthalate, nylon 6, nylon 6,6, cellulose, polypropylene cellulose acetate, polyacrylonitrile and copolymers of polyacrylonitrile as constituents of a second component. Inherently conductive polymers (ICP) such as doped polyanaline or polypyrolle can be incorporated into the conductive layer along with the carbon to complete the formulation. In certain embodiments, the ICP can be used as the electrode surface alone or in conjunction with carbon. The Resistat® fiber is availability in diameters of 0.0025 to 0.016 inches, which is suitable for sensor electrodes configured in accordance with the principles of the present disclosure. Example patents disclosing composite fibers suitable for use in practicing sensor modules configured in accordance with the principles of the present disclosure include U.S. Pat. Nos. 3,823,035; 4,255,487; 4,545,835 and 4,704,311, which are hereby incorporated herein by reference in their entireties.

The sensing layers provided at working electrodes of sensor modules configured in accordance with the principles of the present disclosure can include a sensing chemistry, such as a redox compound or mediator. The term redox compound is used herein to mean a compound that can be oxidized or reduced. Example redox compounds include transition metal complexes with organic ligands.

Preferred redox compounds/mediators include osmium transition metal complexes with one or more ligands having a nitrogen containing heterocycle such as 2,2'-bipyridine. The sensing material also can include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In sensor systems, such as the one being described, these enzymes catalyze the electrolysis of an analyte by transferring electrons between the analyte and the electrode via the redox compound. Further information regarding sensing chemistry can be found at U.S. Pat. Nos. 5,264,105; 5,356,786; 5,262,035; and 5,320,725, which were previously incorporated by reference in their entireties.

During sample analysis (e.g., blood analysis) at one of the analysis zones, a voltage can be applied through the analysis zone between the electrodes 28, 30. When the potential is applied, an electrical current will flow through the fluid sample between the electrodes 28, 30. The current is a result of the oxidation or reduction of an analyte, such as glucose, in the volume of fluid sample located within the analysis zone. This electrochemical reaction occurs via the electron transfer agent in the sensing layer and an optional electron transfer catalyst/enzyme in the sensing layer. By measuring the current flow generated at a given potential (e.g., with a controller described herein), the concentration of a given analyte (e.g., glucose) in the fluid sample can be determined. Those skilled in the art will recognize that current measurements can be obtained by a variety of techniques including, among other things, coulometric, potentiometric, perometric, voltometric, and other electrochemical techniques.

Figure 5:
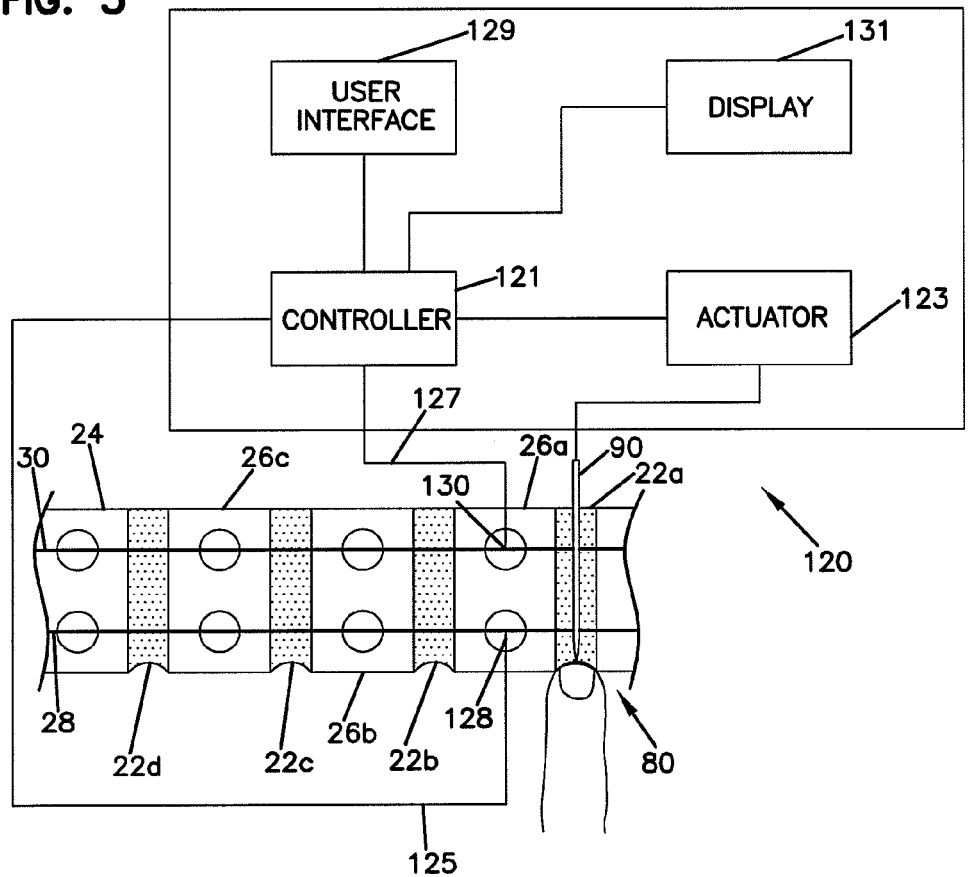
FIG. 5 shows the sensor array and flexible carrier of FIG. 1 incorporated into an analyte monitoring unit/system, the sensor array is being used to analyze a first blood sample at a first analysis zone.

Referring to FIG. 5, the sensor array 20 and carrier 24 are shown incorporated as a sub-component of an analyte monitoring unit 120. The unit 120 includes a holder that houses a controller 122. The housing can also include a holder that holds the sensor array 20 and carrier 24. The housing can further include a drive arrangement for moving the carrier 24 to consecutively index the analysis zones to a use position 80 defined by the unit 120.

In general, the unit 120 includes the controller 121, an actuator 123, and input lines 125, 127 extending from contacts 128, 130. The controller 122 controls the actuator arrangement 123 for disposable driving skin piercing members 90 (e.g., needles, lancets, canulas or like structures) between the retracted and extended positions to obtain a fluid sample (e.g., a blood sample) at the use position 80. The controller 121 can include a microcontroller, a mechanical controller, software driven controller, a hardware driven controller, a firmware driven controller, etc. The controller can include a microprocessor that interfaces with memory.

The input lines 125, 127 carry data/signals/readings (e.g., voltage values) generated between the electrodes 28, 30 at a given one of the analysis zone being used during analysis of a fluid sample to the controller 121 for analysis. The controller 121 converts the data/signals/reading to an analyte concentration level (e.g., a blood glucose reading) or other desired information. The controller 121 causes a display 131 to indicate the processed information to the user. Other information also can be presented on the display 131. In one embodiment, the display 131 is a visual display. In other embodiments, an audio display also can be used. Additional information can be provided to the processor 121 via a user interface 129 (e.g., buttons, switches, etc.).

Figure 6:
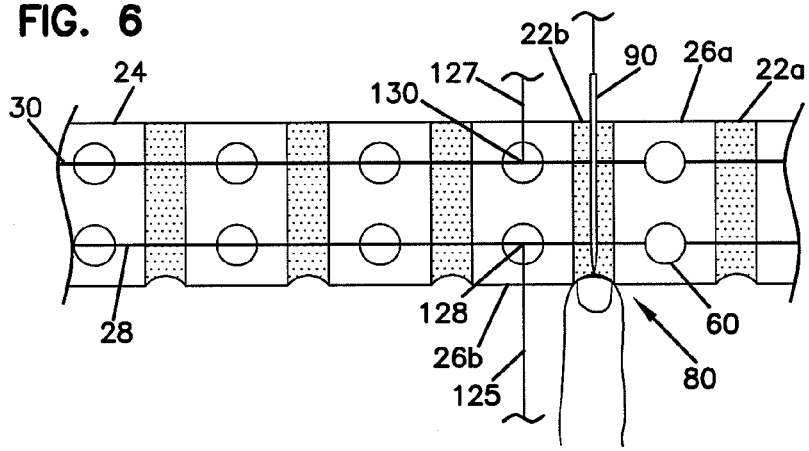
FIG. 6 shows the sensor array being used to analyze a second blood sample at a second analysis zone.

In use of the unit 120, the carrier 24 is indexed to align the analysis zone 22a with the use position 80 of the unit 120 (see FIG. 5). A skin piercing member 90 is then loaded into the unit at the use position 80 and the person places their finger at the indentation 40 corresponding to the analysis zone 22a. The actuator 123 then extends the skin piecing member 90 causing a sample site at the finger in the form of a puncture wound. Blood from the sample site wets the analysis zone 22a and flows by capillary action across the analysis zone 22a. The contacts 128, 130 are placed in electrical contact with the electrodes 28, 30 at the gap 26a. The controller 121, via the lines 125, 127 and contacts 128, 130, then causes a voltage to be applied between the electrodes 28, 30 and across the wetted analysis zone 22a. The controller 121 then takes a reading and determines an analyte (e.g., glucose) concentration in the blood sample. Once the reading has been taken, the skin piercing member 90 can be disposed of and the carrier is indexed such that the analysis zone 22b and the gap 26b are positioned at the use position 80 (see FIG. 6). In the use position 80, the contacts 128, 130 engage the electrodes 28, 30 at the gap 26b. Also, the controller 121 can actuate a punch which severs the electrodes 28, 30 at the gap 26a such that the used/wetted analysis zone 22a is electrically isolated from the portions of the electrodes 28, 30 traversing the unused analysis zones 22b-22d.

Figure 7:
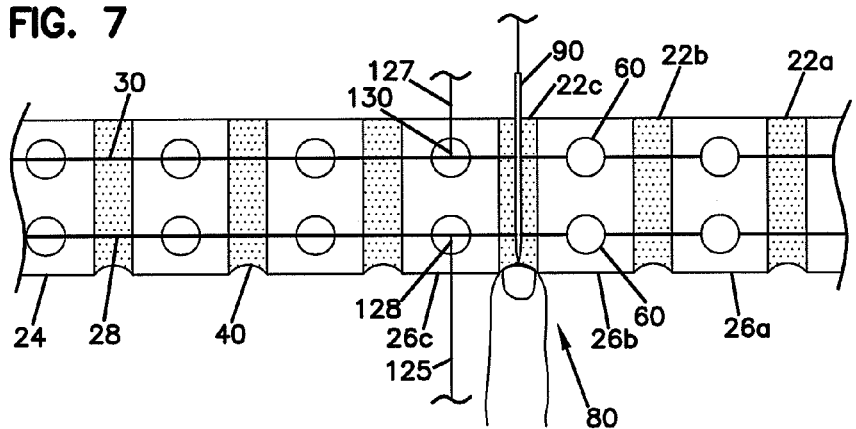
FIG. 7 shows the sensor array being used to analyze a third blood sample at a third analysis zone.

To analyze a second blood sample, a new skin piercing member 90 is loaded into the unit and the process is repeated causing the analysis zone 22b to be wetted with the second blood sample. A voltage is then applied between the electrodes 28, 30 and across the analysis zone 22b and a reading is taken. Once the reading has been taken, the skin piercing member 90 can be disposed of and the carrier is indexed such that the analysis zone 22c and the gap 26c are positioned at the use position 80 (see FIG. 7). In the use position, the contacts 128, 130 engage the electrodes 28, 30 at the gap 26c. Also, the controller 121 can actuate a punch which severs the electrodes 28, 30 at the gap 26b such that the used/wetted analysis zone 22b is electrically isolated from the portions of the electrodes 28, 30 traversing the unused analysis zones 22c-22d.

Figure 8:
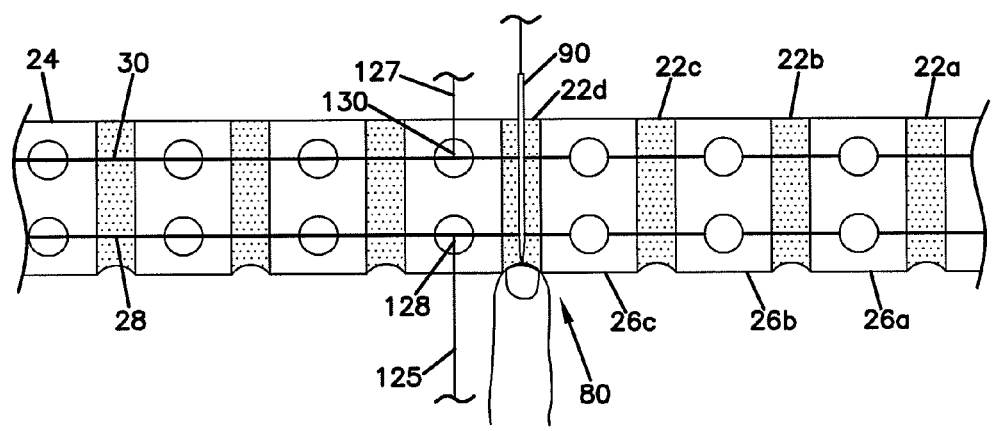
FIG. 8 shows the sensor array being used to analyze a fourth blood sample at a fourth analysis zone.

To analyze a third blood sample, a new skin piercing member 90 is loaded into the unit and the process is repeated causing the analysis zone 22c to be wetted with the third blood sample. A voltage is then applied between the electrodes 28, 30 and across the analysis zone 22c and a reading is taken. Once the reading has been taken, the skin piercing member 90 can be disposed of and the carrier is indexed such that the analysis zone 22d and the gap 26d are positioned at the use position 80 (see FIG. 8). In the use position, the contacts 128, 130 engage the electrodes 28, 30 at the gap 26d. Also, the controller 121 can actuate a punch which severs the electrodes 28, 30 at the gap 26c such that the used/wetted analysis zone 22c is electrically isolated from the portions of the electrodes 28, 30 traversing the unused analysis zones 22d. Analysis zone is then ready for use as described above. Moreover, it will be appreciated that the process can be consecutively repeated until all of the analysis zones on the carrier have been used. Thereafter, the carrier 24 can be disposed of and replaced with a like carrier having unused analysis zones.

Figure 9:
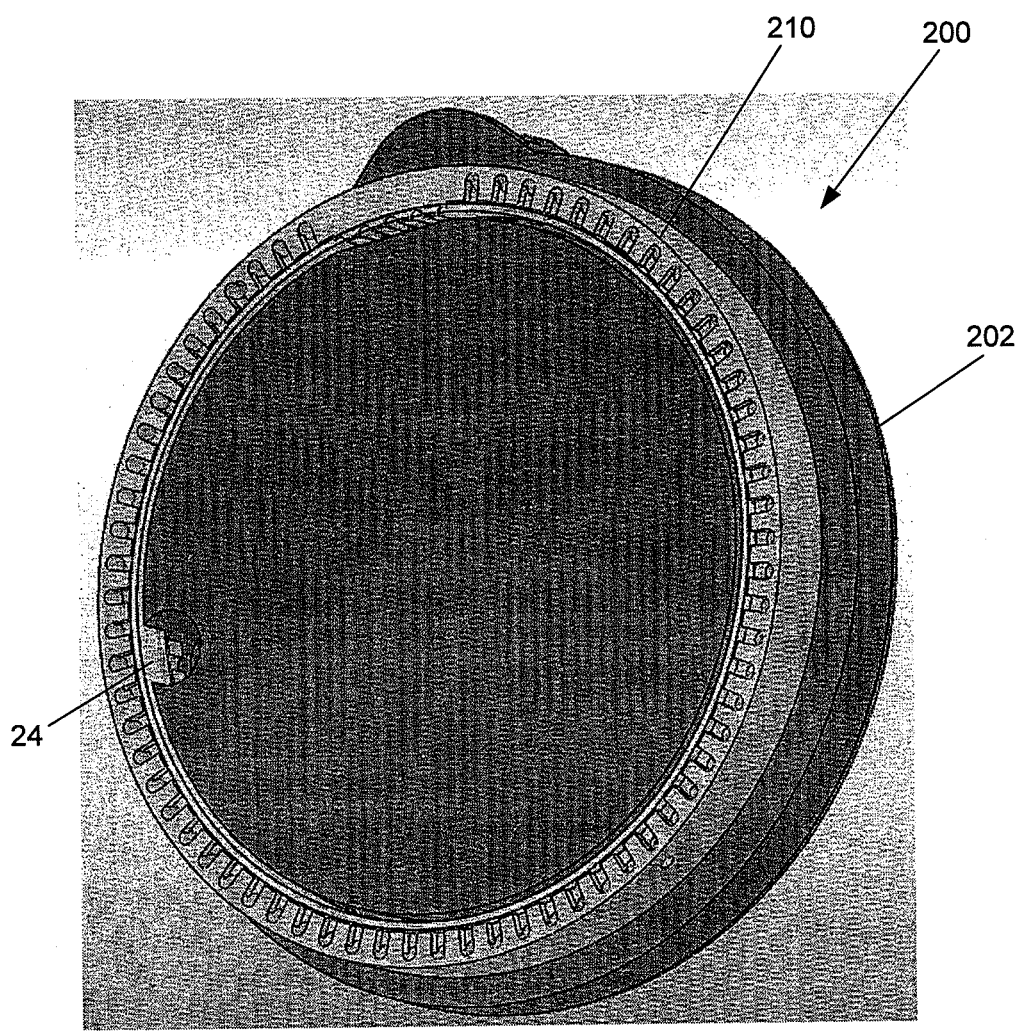
FIG. 9 shows an analyte monitoring unit adapted for use with the sensor array and flexible carrier of FIG. 1.
Figure 10:
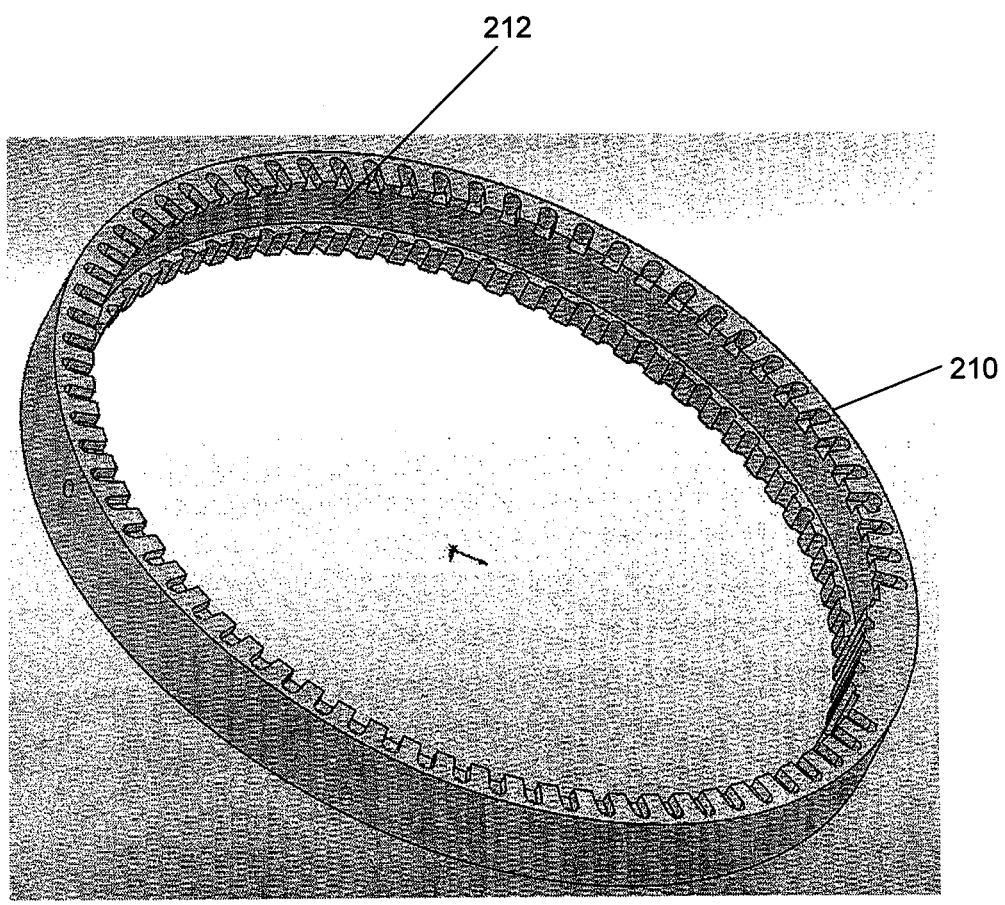
FIG. 10 shows a drive gear of the analyte monitoring unit of FIG. 9.
Figure 11:
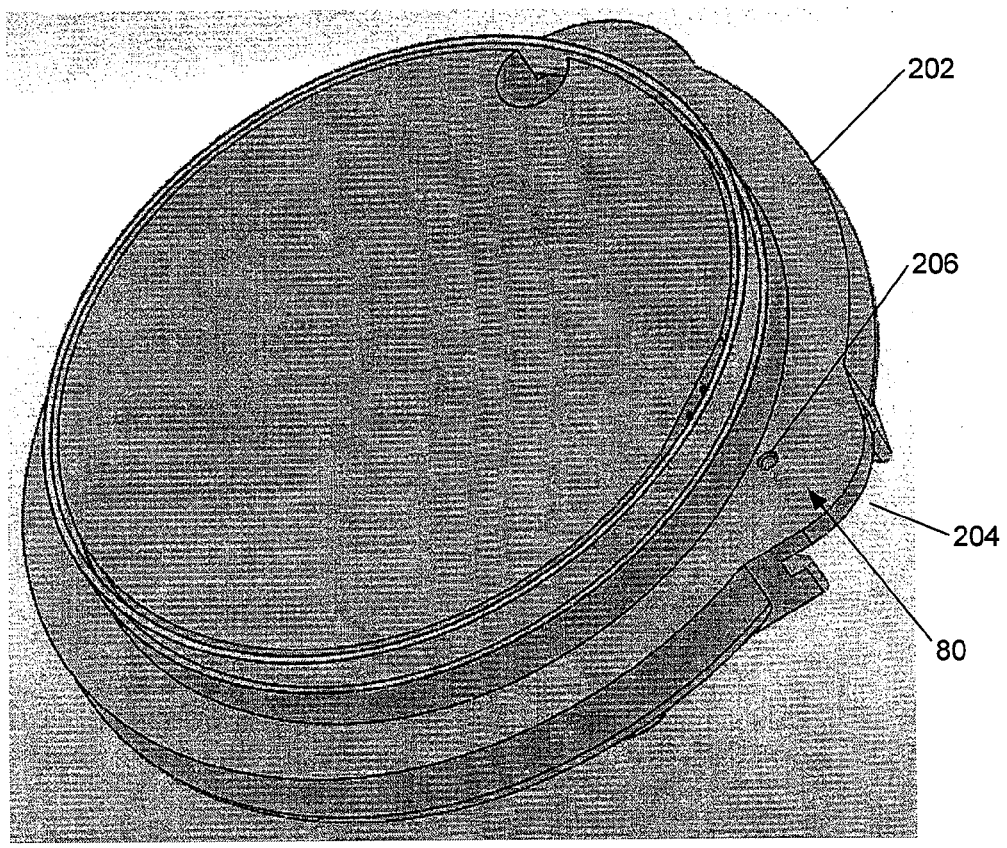
FIG. 11 shows a portion of the analyte monitoring unit of FIG. 9 after the drive gear has been removed.

FIGS. 9-11 show a hand-held analyte monitoring unit 200 that can be used with the sensor array 20 and carrier 24 of FIG. 1. The unit 200 includes a main housing 202 in which a controller can be housed. The main housing 202 can also include an indexing drive. A display and a user interface can be provided on the back side of the main housing 202. The main housing 202 includes a use location 80 (i.e., a sampling location) defining a rear receptacle 204 for mounting a skin piercing member actuator. The skin piercing member actuator is adapted to extend a skin piercing member through an opening 206 at the use location 80. The unit 200 also includes a drive gear 210 that mounts on the main housing 202 and is rotated by the indexing drive to index the carrier 24 to consecutively move unused analysis zones to the use location 80. The drive gear 210 includes an inner cylindrical surface 212. The carrier 24 is rolled/wrapped in a cylinder and secured to the cylindrical surface 212. The drive gear/drive ring can be disposable and the carrier can be pre-attached to the drive gear at the manufacturing facility or elsewhere before purchase by a consumer.

In alternative embodiments, only one of the electrodes 28, 30 may be severed to isolate used/spent analysis zones from unused analysis zones. By severing at least one of the electrodes 28, 30 at a gap between the used/spent analysis zone and the unused analysis zones, a voltage/potential is prevented from being applied across the used/spent analysis zone when a subsequent analysis zone is being used to analyze a fluid sample.

The invention claimed is:

1. A sensor apparatus comprising:
    a flexible carrier that is elongated along a length of the carrier;
    a plurality of analysis zones carried by the carrier, the analysis zones being spaced-apart from one another along the length of the carrier; and
    first and second spaced-apart electrodes carried by the flexible carrier, the first and second electrodes having lengths that extend along the length of the carrier, at least one of the first and second electrodes including analyte sensing chemistry, the first and second electrodes extending across and contacting the plurality of analysis zones;
    wherein the carrier defines grooves in which the first and second electrodes are mounted.

2. The sensor apparatus of claim 1, wherein the plurality of analysis zones are formed by recesses in the flexible carrier, the recesses being positioned below the first and second electrodes.

3. The sensor apparatus of claim 2, wherein the recesses extend across a width of the carrier.

4. The sensor apparatus of claim 3, wherein the plurality of analysis zones include capillary flow enhancing structures positioned within the recesses for encouraging capillary flow across the width of the carrier.

5. The sensor apparatus of claim 4, further comprising punch holes defined through the carrier at a location between the analysis zones, wherein the electrodes extend across the punch holes.

6. The sensor apparatus of claim 4, wherein the carrier includes a side surface defining indentations at each of the analysis zones.

7. A sensor apparatus comprising:
    a flexible carrier that is elongated along a length of the carrier;
    a plurality of analysis zones carried by the carrier, the analysis zones being spaced-apart from one another along the length of the carrier; and
    first and second spaced-apart electrodes carried by the flexible carrier, the first and second electrodes having lengths that extend along the length of the carrier, at least one of the first and second electrodes including analyte sensing chemistry, the first and second electrodes extending across and contacting the plurality of analysis zones;
    wherein the plurality of analysis zones are formed by recesses in the flexible carrier, the recesses being positioned below the first and second electrodes, wherein the recesses extend across a width of the carrier, and wherein the plurality of analysis zones include capillary flow enhancing structures positioned within the recesses for encouraging capillary flow across the width of the carrier.

8. The sensor apparatus of claim 7, further comprising punch holes defined through the carrier at a location between the analysis zones, wherein the electrodes extend across the punch holes.

9. The sensor apparatus of claim 7, wherein the carrier includes a side surface defining indentations at each of the analysis zones.

* * * * *